United States Patent [19]

Schmid et al.

[11] 4,391,522
[45] Jul. 5, 1983

[54] TEST APPARATUS FOR DETERMINING RESISTANCE TO LIGHT AND WEATHER INFLUENCES

[75] Inventors: Helmut Schmid, Krefeld; Martin Bock, Duisburg; Günther Kämpf, Krefeld, all of Fed. Rep. of Germany

[73] Assignee: Original Hanau Heraeus GmbH, Hanau, Fed. Rep. of Germany

[21] Appl. No.: 193,465

[22] Filed: Oct. 3, 1980

[30] Foreign Application Priority Data

Oct. 4, 1979 [DE] Fed. Rep. of Germany ....... 2940325

[51] Int. Cl.³ .......................... G01N 17/00; G01J 3/38
[52] U.S. Cl. ................................. 356/326; 73/150 R; 356/328
[58] Field of Search ............... 356/326, 328, 332, 334; 250/365, 372; 73/150, 159

[56] References Cited

U.S. PATENT DOCUMENTS

| | | | |
|---|---|---|---|
| 3,224,266 | 12/1965 | Klippert | 73/150 |
| 3,360,650 | 12/1967 | Lawrence | 250/372 |
| 3,576,125 | 4/1971 | Kockott et al. | 73/150 |
| 3,686,940 | 8/1972 | Kockott | 73/159 |
| 3,693,020 | 9/1972 | Ackerman, Jr. | 250/372 X |
| 4,012,147 | 3/1977 | Walrafen | 356/301 X |
| 4,279,511 | 7/1981 | Maute et al. | 356/334 X |

Primary Examiner—F. L. Evans
Attorney, Agent, or Firm—Frishauf, Holtz, Goodman & Woodward

[57] ABSTRACT

To provide for more reliable determination of resistance of sample surfaces to light and weather influences, test apparatus is equipped with a radiation-measuring device. A portion of radiation used for testing is guided to the measuring device, by quartz guides, spectrally dispersed, and measured as to intensity and/or dosage in one or several pre-selected spectral regions. Tests may use natural or artificial radiation, and a measuring device may be stationary or movable relative to a radiation source.

5 Claims, 8 Drawing Figures

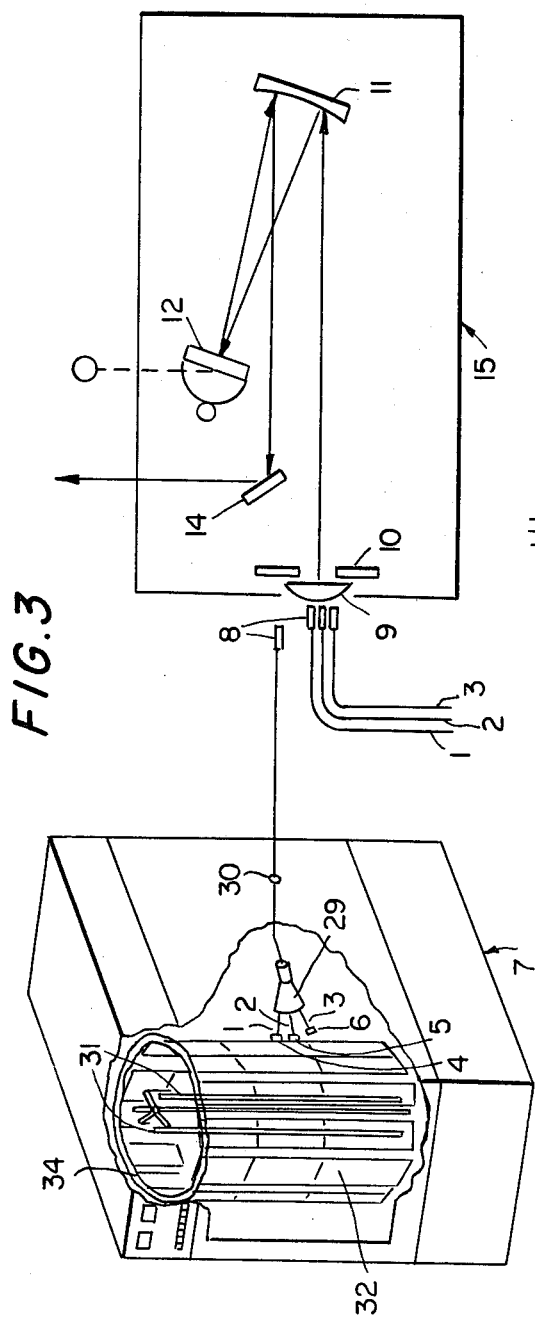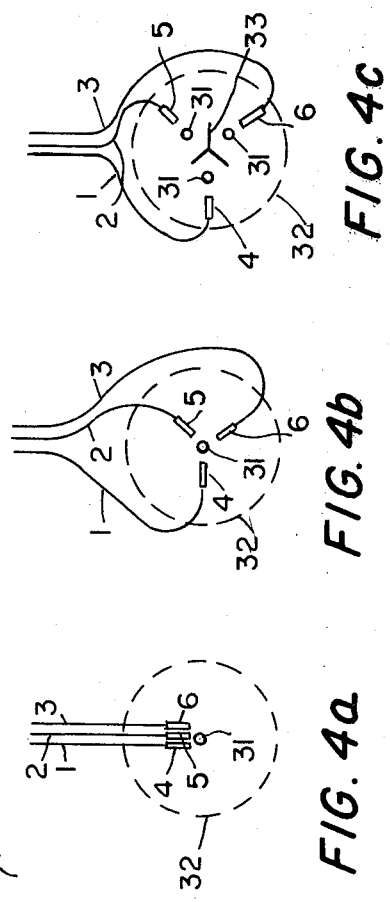

TEST APPARATUS FOR DETERMINING RESISTANCE TO LIGHT AND WEATHER INFLUENCES

This invention is concerned with test apparatus for determining resistance to light and weather effects on inorganic or organic pigments, plastics or lacquers. More particularly, such apparatus may include a chamber with at least one radiation source and at least one fastening arrangement for a sample which at least in part consists of a material to be tested.

BACKGROUND AND PRIOR ART

Testing of inorganic and organic pigments, plastics, or lacquers with regard to resistance to action of light and weather may involve exposing samples to naturally occurring light and weather conditions. Alternatively, to shorten the test period, exposure may be by means of apparatus for accelerated weathering having a high-intensity radiation source which typically has an enhanced ultraviolet component. In either case it has become apparent that mere correlation of test results to duration of exposure leads to widely scattered results, due mainly to variation in light intensity and spectral composition during sample exposure. In particular, meaningful comparison of test results is often impossible when test apparatus for accelerated weathering of different design are used, especially when different radiation sources are involved such as, e.g., carbon arc, xenon, mercury vapor, or fluorescent lamps.

In known radiation measuring devices various filters may be interposed between a radiation source and a radiation detector, thereby providing means for recognizing (at least qualitatively) changes of the radiation used in one or another of selected narrow spectral ranges. In one such known device, an exchangeable filter can be interposed between a radiation source and a radiation detector. In another, well-known radiation intensity measuring device, three different filters are interposed in consecutive time periods, and the radiation intensities of the three corresponding wavelength intervals are measured in turn. Both devices are suitable only for the determination of radiation from xenon arc lamps.

Such devices are insufficient for several reasons. It is known that the decomposition behavior of binders or pigments is strongly dependent on the spectral composition of incident light. Accordingly, there is a need to expose samples to radiation which is tuned to the photoactive region of such binder and/or pigment. This, in turn, calls for a radiation intensity measuring device which is selectively sensitive to one or several desired spectral regions.

Furthermore, uniformity of sensitivity in a spectral region is not assured in known devices; intensive irradiation tends to cause unnoticed and uncontrollable changes in the properties of bell-jar and interference filters. Such changes lead to considerable uncertainity as to just how much radiation the samples were exposed to and this, in turn, results in the well-known, undesirably wide range of scattering of measured values obtained from test apparatus, especially when measurements of intensity are made in the ultraviolet spectral region (which here is of special interest).

If a device includes only one filter, no detailed information is obtained about intensity as differentiated according to wavelength of radiation incident on a sample. If, however, a device includes three filters, filter changing may preclude reliably taking account of short-term variations of radiation intensity.

In practice, exposure time is often used instead of radiation dosage as a measure of readiation incident on the samples. This method depends on constancy of distribution of radiation and constancy of intensity of the radiation sources (i.e., ambient radiation under natural conditions and artificial radiation under accelerated test conditions); such constancy is usually not assured in practice.

THE INVENTION

It is an object of the invention to provide for test apparatus for determining resistance to action of light and weather, such apparatus having an adaptable radiation measuring device (i.e., a device having one or several sensitive ranges which can be adjusted to coincide with one or several ranges which are optimal for irradiating the samples). As a benefit of the invention, testing may proceed without recalibration and adjustment of test apparatus in the course of irradiation.

In accordance with the invention, the radiation intensity measuring device includes means for the spectral dispersion of radiation and means for detecting radiation which are adjustable so as to permit measurement of radiation intensity and/or dosage in at least two specifiable spectral regions, radiation typically being ultraviolet radiation emitted by a radiation source and transmitted by a light guide.

A radiation detector may advantageously consist of an array of photodiodes. It is advantageous further if several light guides, originating from several points in the test apparatus, lead to the radiation measuring device input, where the combined radiation from light guides can be measured in a desired spectral range. This allows for averaging inhomogeneously distributed radiation in a test apparatus. Furthermore, such a measuring device may be used in test apparatues having more than one radiation source. Also, it is advantageous if, in addition to radiation dosage integrated over time and/or specified spectral ranges, it is possible to obtain a reading of instantaneous radiation intensity.

If spectral dispersion in the radiation detector is produced by means of an element which is resistant to radiation (such as, e.g., a prism or a grating), constancy of sensitivity and spectral constancy of the radiation measuring device are assured. Preferred, in particular, is a reflection grating. By the provision of one or several radiation detectors which are adjustable, it is assured that radiation which is optimal for a test is in fact measure. Substantial advantages, especially with respect to testing methodology, are realized if a second or additional radiation detector is used to measure incident radiation in a spectral region which differs from the region which is optimal for testing a binder or a pigment. For example, a second or additional detector may be tuned to a spectral region which is defined by a recognized standard. Similarly, a measured value may be related to other values of the spectral region, whereby, in particular, connection may be made to other test series. Furthermore, changes of the intensity in different spectral regions can provide information about aging of the radiation source. The photodetectors are chosen sensitive preferably to wavelengths in the range of 300 nm to 700 nm and preferably in the range of 300 nm to 450 nm.

In addition to measurement of radiation dosage based on integration of intensity apparatus in accordance with the invention conveniently allows for measurement of instantaneous radiation intensity without interference with the measurement of radiation dosage.

Apparatus in accordance with the invention may conveniently be provided with a mechanical device for lateral displacement of the photodetectors in the image plane of a slit, so as to optimally adjust the apparatus at the beginning of a test. Since the active part of an array of photodiodes (as is particularly suited for photodetection) may be laterally displaced over the entire array by switching, it is usually not necessary to displace the array mechanically. Rather, it suffices to appropriately select signals from individual groups of photodiodes as determined, e.g., by the orientation of a grating to a detector. Such array of diodes further permits, e.g., the convenient measurement of the spectrum of a radiation source in the course of an experiment; this may provide for early and positive warning of deterioration due to aging of a radiation source and of frequently employed radiation conversion filters.

It is understood that the radiation measuring device in accordance with the invention may also be designed in the form of a battery-operated device. The electronic components preferably consist of an energy-saving integrated complementary metal oxide-silicon (C-MOS) circuit in combination with a surveillance and alarm circuit for alerting of low battery voltage. The device may be constructed on a very small scale.

The radiation dosage per unit area which is incident on a sample varies spatially and over time in known apparatus for testing for light and weather resistance. As a result, unevenly distributed deposits form on the radiation source and the radiation conversion filters.

Time variations and spatial variations of radiation intensity are particularly pronounced in the case of carbon arc radiation sources. These devices typically include three radiation sources of which only one is active at any one time. During short transition periods, the radiation from the source being started deviates from the statistical norm.

For the sake of compensation of such variations, it is known to change the position of samples according to a specified schedule. In accordance with an embodiment of the invention, spatial variations can be averaged out. To this end, light guides are placed at several points in the apparatus, and their combined output is made incident on the slit of the measuring device; optical components of the apparatus ensure that all light coming from the several wave guides is taken into account and measured.

In accordance with an embodiment of the invention, the measuring device is attached, e.g., in lieu of to one or several samples, to a carousel or rotary support means. In the course of routine rearrangement of samples, the measuring device, too, changes place. Due to the use of light guides, the space required for the measuring devices (the width of the cross-sectional area to be tested) can be kept small (e.g., 1 cm to 3 cm). In such apparatus, complete averaging of radiation is possible over time as well as spatially (horizontally as well as vertically).

Such complete averaging is required especially in the case of radiation dosimetry in apparatus equipped with a carbon arc radiation source; in apparatus equipped with xenon arc or mercury vapor radiation sources, light guides are usually sufficient which are spatially fixed in the apparatus. (This is the case especially when carefully selected lamps are used whose shape is fixed within narrow limits).

On account of most precise measurement of incident radiation, an advantage realized in accordance with the invention lies in a considerably reduced range of scattering of test results when testing is under natural conditions and, especially, when different apparatus for accelerated weathering is used, and when the same apparatus is used at different occasions.

THE DRAWINGS

FIG. 3 shows, in a fashion similar to FIG. 1, an alternate embodiment of test apparatus in accordance with the invention;

FIG. 4a through 4c show embodiments of different associations of radiation source or sources and radiation detectors;

DESCRIPTION OF THE ILLUSTRATED EMBODIMENTS

Figure 1:
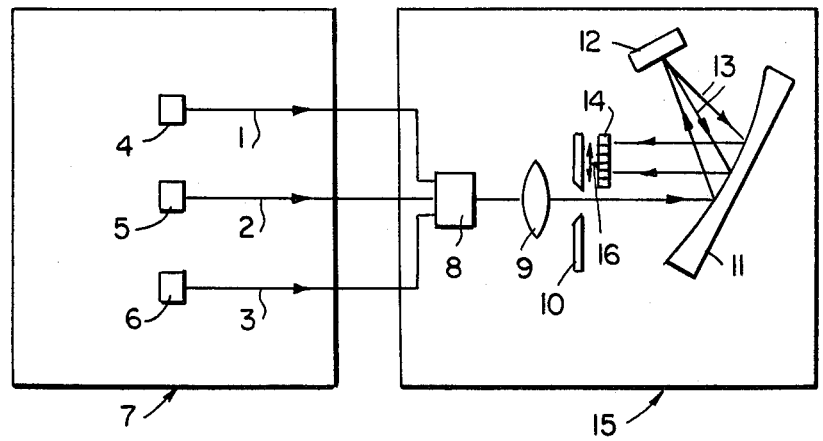
FIG. 1 shows test apparatus for determining resistance to light and weather influences equipped with a radiation measuring device with schematically indicated light paths.

In FIG. 1, three quartz light guides 1, 2, and 3 originate at different terminal positions 4, 5, and 6, respectively, in the vicinity of test samples in apparatus for determining resistance to light and weather influences. Light guides 1, 2 and 3 are combined into a bundle at point 8; the combined light traverses a quartz lens 9 and a slit 10 and is reflected by a concave mirror 11 on a reflection grating 12. Spectrally decomposed ratiation is again reflected by mirror 11 and reaches photodetector 14 which consists of an array of photodiodes (optionally mechanically movable by adjusting means 16). Light paths are shown merely in a schematic fashion; the presence of diaphragms and scattered light filters in enclosure 15 is known to a person skilled in the art.

Figure 2:
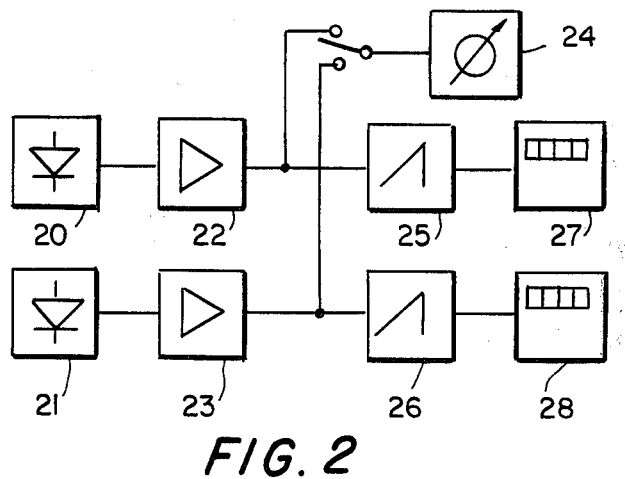
FIG. 2 is a block circuit diagram of the components of a radiation measuring device, starting with the radiation detector and proceeding through indication or recording.

FIG. 2 shows the path of electrical signals. Signals originate from two specifically selected photodiodes 20 and 21 of the array 14 of photodiodes and are amplified by amplifiers 22 and 23, respectively. An indication of radiation intensity in a spectral range as a function of time may be indicated by display instrument 24. The signals from diodes 20 and 21 reach integrators 25 and 26, respectively. Upon reaching a predetermined value, an impulse is produced by a toggle stage, and a count is increased by one one in counter 27 or 28, respectively. If signal strength is sufficiently high, integration may be by an analogue technique; otherwise, digital integration is preferable in the interest of achieving a desired accuracy. If the measuring device is battery powered, a surveillance and alarm circuit is conveniently made integral to the device for detecting low-voltage conditions.

FIG. 3 shows enclosure 7 and several light guides 1, 2, and 3 originating from fixed terminal points 4, 5, and 6 in chamber 7. Light guides 1, 2, and 3 may be located at different positions with respect to one or several radiation sources as shown, more particularly, in FIG.

4a, 4b, and 4c. The samples 32 may be arranged surrounding a central light source 31 (e.g., equidistant from the source) or, as shown in FIG. 3 and 4c, they may be associated with three different light sources 31 which are situated in a central area. Samples may be fixed or movable as, e.g., on a motor-driven carousel. The light guides 1, 2, and 3 may be spaced vertically as shown in FIGS. 1 and 3 and/or circumferentially as shown in FIGS. 4b and 4c.

The quartz light guides 1, 2 and 3 are associated with different positions 4, 5 and 6, e.g., near elongated, flat test samples 32. The light guides are combined into a bundle, e.g., in an optical coupler 29 and pass in a light guide cable, through opening 30 in the wall of chamber 7, to the radiation measuring device.

The arrangement of radiation sources and of associated mirrors is described, in detail, in U.S. Pat. No. 3,686,940, issued Aug. 29, 1972, to D. Kockott and in U.S. Pat. No. 3,576,125, issued Apr. 27, 1971, to D. Kockott et al. Devices and arrangements described there may also be used in apparatus of the present invention; this applies not only to radiation sources and mirrors, but also to the arrangement of samples on a carousel and to their motor drive as described in U.S. Pat. No. 3,224,266, issued Dec. 21, 1965, to H. U. Klippert. These patents are hereby incorporated by reference for the sake of example and without limitation thereto.

Designation 33 refers to selectively reflective mirrors for ultraviolet radiation and light; designation 34 refers to sample support means. Apparatus in accordance with the invention typically comprises power supply means and may further comprise memory means and information display means (not shown).

Figure 5:
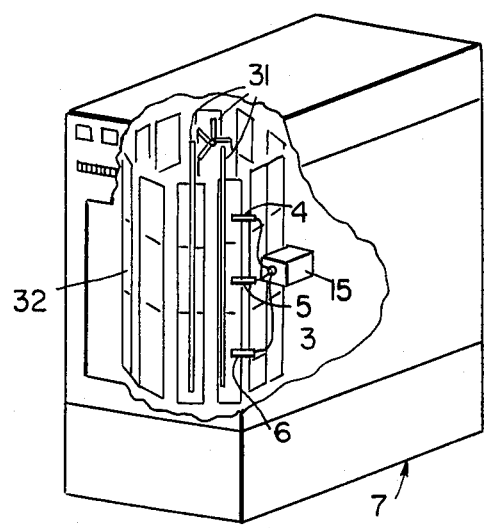
FIG. 5 shows an apparatus having a rotary sample holder or carousel.

In an alternate embodiment in accordance with FIG. 5, a carousel in chamber 7 carries test samples 32, space being reserved on the carousel for light input terminals 4, 5 and 6 of light guides 1, 2, and 3, respectively. The light guides terminate at the radiation measuring device 15 which may be attached, e.g., about half-way up, to a support plate occupying the space of a sample so as to be readily carried along by the carousel. Alternate spatial arrangements are not precluded.

Figure 6:
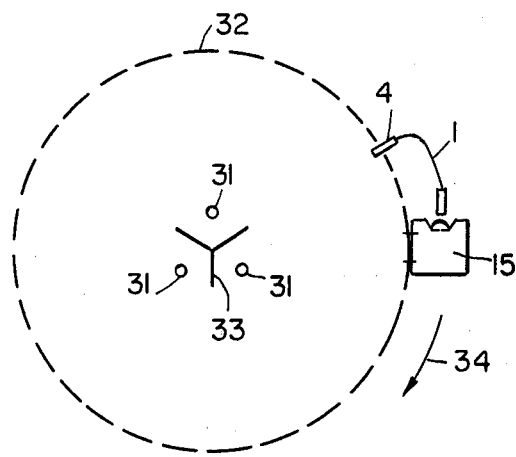
FIG. 6 is a plan view of the apparatus of FIG. 5.

FIG. 6 shows, in plan view, the apparatus according to FIG. 5, sense of rotation of the carousel being indicated by arrow 34. In a fashion similar to FIG. 3, light guides leading from various points of a sample surface space may be connected to a single light guide which, in turn, guides the combined light to the radiation measuring device 15.

EXAMPLE 1

Device for measuring radiation intensity and dosage in apparatus for accelerated weathering with a xenon lamp of 5000–6500 watt as a light source.

The radiation emitted by the lamp is guided to the measuring instrument by a quartz light guide having a length of 530 mm and a diameter of 10 mm. The light receiving terminal of the light guide is at a distance of approximately 340 mm from the focus of the radiator. The measuring instrument includes, among its optical components, a bioconvex lens (f=30 mm), a slit width approximately 5 mm, a concave mirror (f=175 mm), a planar, rotatably disposed reflection grating (1440 lines per mm; blazed area=25 mm by 20 mm), and twin receivers. Bandwidth is adjusted to 7 nm in each receiver. The necessary suppression of scattered light to below 1 percent at a wavelength of 340 nm is effected by a scattered light filter and numerous diaphragms.

The output signals of the twin photodiode receivers (Linear Array LD2-1, Centronic, USA) are pre-amplified (AD503KH, Analog Devices, USA), post-amplified (AD308, Analog Devices, USA), integrated, and optionally displayed directly. A digital voltmeter (Elektro Numerics, USA) is used for the direct display of radiation intensity; this instrument is calibrated in $W/m^2/nm$ and has a range of 10 V. The integration of the radiation intensity is by means of an integrator (AD503KH, Analog Devices, USA, in combination with a 10 microfarad condenser MKB-1, Wima, Mannheim, Germany). A mechanical, six-place pulse counter is used for the display of radiation dosage. The instrument is connected to a highly stabilized power supply device ($\pm 15$ V, 100 mA; Oltronix, USA).

EXAMPLE 2

Testing of the stability of a measuring device according to the invention as compared with a commercially available device (Weather-O-Meter ®).

For testing of long-term stability, both devices were placed in apparatus for accelerated weathering equipped with a 6500 watt xenon lamp. The comparison was made at a central wavelength of approximately 340 nm, and the measuring devices were continuously exposed to ultraviolet radiation. To check stability, the lamp was replaced for a short period by a calibrated radiation source. Radiation intensity (as indicated by the device according to the invention over a period of three months) was constant to within $\pm 2.8$ percent. However, over a period of just one month, the reading of the commercial device was down 12 percent.

A check of the transmissivity of the bell jar filter incorporated in the apparatus showed a decrease of transmissivity of 19 percent and a shift of the wavelength of maximum transmissivity by 2 nm.

After six months of uninterrupted use, the filter showed considerable additional decrease of transmissivity ($-69$ percent).

EXAMPLE 3

Test of the change of intensity as a function of wavelength of xenon lamps in apparatus for accelerated weathering.

The tests were made using an instrument in accordance with the invention having a bandwidth of 7 nm at three selected wavelengths of 340 nm, 370 nm, and 520 nm.

Radiation sources of the same type and the same power (e.g., 6500 watt) showed variations in radiation intensity of up to 20 percent indepent of wavelength. By adjusting power input to a radiation source, emission as measured by the measuring device could be matched to the emission of a radiation reference source. However, after 3000 hours of operation, the emission spectrum of the adjusted radiation source had changed, intensity having dropped by 22 percent of a wavelength of 520 nm, by 45 percent at a wavelength of 340 nm, and by 37 percent at a wavelength of 370 nm. Decrease in radiation intensity was even more pronounced in the spectral region below 340 nm (which is particularly important for testing light and weather influences).

EXAMPLE 4

Use of the radiation measuring device in apparatus for accelerated weathering employing a carbon arc radiation source.

Apparatus for accelerated weathering typically includes three carbon arc radiation sources. Commercially available instruments are not suited for radiation dosimetry. The emission of a selectively operating carbon arc radiation source cannot be measured with sufficient accuracy by a single, fixed light guide; at least three such light guides, frosted on both sides, are necessary for radiation dosimetry. However, such a device did not meet thee customarily required accuracy of ±5 percent. This requirement was met only by a device which was carried movably alongside with a sample and equipped with two-sided frosting of light guides for vertical averaging of radiation incident on a sample.

EXAMPLE 5

Use of the radiation measuring device under natural conditions of light and weather.

Upon adjustment of sensitivity by approximately an order of magnitude, a radiation measuring device in accordance with the invention can be used for dosimetry under naturally occurring conditions of light and weather. To compensate for the cosine distribution of light indicent on a flat sample surface, a set of frosted light guides is used which are arranged at different angles to such surface.

We claim:

1. Apparatus for determining resistance to light and weather influences of sample surfaces, said apparatus including, in combination, with at least one source of light disposed for irradiation of said sample surfaces:

fastening means (34) for fastening at least one sample for a period of time during which radiation from said source is incident on at least a portion of the surface of said sample, radiation measuring means (15) comprising radiation detection means (14) and radiation indicating means (24; 27,28), and light guiding means (1, 2, 3; 29; 8; 9), having a plurality of input terminals, each in the vicinity of one of said fastening means (34), for guiding a portion of the radiation of said at least one light source from said input terminals to said radiation measuring means (15), said input terminals being disposed for receiving radiation from said at least one light source comparable with the radiation incident on portions of said at least one sample respectively adjacent to said input terminals, wherein, in accordance with the invention, said radiation measuring means (15) comprises, means (12) for producing a spectral dispersion of radiation received from said light guiding means and thereby making spectrally dispersed radiation incident on said radiation detection means (14), and means (16) for adjusting said radiation detection means so as to selectively detect radiation in at least one of a plurality of spectral regions.

2. Apparatus of claim 1 in which said radiation detection means is an array of photodiodes.

3. Apparatus of claim 1 in which said light-guiding means comprises a plurality of light guides and means for combining radiation propagating in said light guides.

4. Apparatus of claim 1 comprising a plurality of said light radiation sources, said light guides having input terminals which are disposed so that radiation from each radiation source reaches at least one light-guide terminal.

5. Apparatus of claim 1 comprising rotation means for rotating said fastening means around said light source, said input terminals being fixedly attached to said rotation means so as to take part in the rotation of said fastening means.

* * * * *